United States Patent [19]

Rodriquez et al.

[11] Patent Number: 5,286,484
[45] Date of Patent: Feb. 15, 1994

[54] **NUCLEOTIDE SEQUENCE CODING FOR AN OUTER MEMBRANE PROTEIN FROM *NEISSERIA MENINGITIDIS* AND USE OF SAID PROTEIN IN VACCINE PREPARATIONS**

[75] Inventors: Silva Rodriquez; Selman H. Sosa; Guillén Nieto; Saturnino H. Martinez; Julio R. F. Masó; Lidia I. N. Pérez; Juan M. Grillo; Vivian M. Córdova; Sonia G. Blanco; Beatriz T. Santos; Jesûs A. del Valle Rosales; Evelin C. Menéndez; Anabel A. Acosta; Edelgis C. Rodriquez; Silian C. León; Alexis M. Lasa, all of Ciudad de la Habana, Cuba

[73] Assignee: Centro de Ingenieria Genetica y Biotecnologia, Cuba

[21] Appl. No.: 754,918

[22] Filed: Sep. 5, 1991

[30] Foreign Application Priority Data

Jul. 9, 1990 [CU] Cuba .................................. 145/90

[51] Int. Cl.$^5$ ...................... A61K 39/02; A61K 39/00; C07H 15/12; C12P 21/06
[52] U.S. Cl. ................................ 435/252.33; 424/92; 536/23.7; 435/69.1; 435/320.1; 530/350
[58] Field of Search ................... 536/27; 530/350; 424/92; 435/69.1, 252.3

[56] References Cited

FOREIGN PATENT DOCUMENTS 0301992 1/1989 European Pat. Off. ... A61R 39/095

*Primary Examiner*—Christine M. Nucker
*Assistant Examiner*—H. Sidberry
*Attorney, Agent, or Firm*—Peter L. Michaelson; Edward M. Fink

[57] ABSTRACT

The present invention is concerned with a method for the isolation of a nucleotide sequence which codes for a protein having a molecular weight of about 64,000 daltons, which is located on the outer membrane of *N. meningitidis*, as well as with the recombinant DNA obtained therefrom, which is used for the transformation of a host microorganism. The technical object pursued with the invention is the identification of a nucleotide sequence coding for a highly conserved and common protein for the majority of pathogenic Neisseria strains, the production of this protein with a high level of purity and in commercially useful amounts using the recombinant way, so that it can be used in diagnostic methods and vaccine preparations with a broad immunoprotection spectrum.

12 Claims, 3 Drawing Sheets

S.SalI ; E. EcoRV ; Ec. EcoRI ; C. ClaI ;
X. XhoI ; H. HindIII ; K. KpnI .

NUCLEOTIDE SEQUENCE CODING FOR AN OUTER MEMBRANE PROTEIN FROM *NEISSERIA MENINGITIDIS* AND USE OF SAID PROTEIN IN VACCINE PREPARATIONS

The present invention is in the field of Genetic Engineering and Biotechnology. More in particular, the invention is related to a nucleotide sequence obtained from the pathogenic bacterium *Neisseria meningitidis*, which nucleotide sequence codes for a protein belonging to the outer membrane of said bacterium. Said protein is cloned and expressed in the host *Escherichia coli*. The characteristics of this protein as well as its capacity to induce immunologically active antibodies (bactericidal antibodies) in its natural host, allow its use in vaccine preparations against pathogenic strains of this microorganism.

The gram-negative bacterium *N. meningitidis* is responsible for one of every three cases of bacterial meningitidis in the world. It was described for the first time by Anton Weichselbaum in 1887 (I. DeVoe, 1982, Microbiol. Revs. 46: 162-190), and man (i.e. human beings) is its only natural host up to date.

In the first half of this century some essential aspects were found in relation to the metabolism and serological differentiation of this microorganism. The first unsuccessful attempts to obtain vaccine preparations were based on its capsular polysaccharide (E. Kabat et al., 1945, J. Exp. Med. 80: 299-307). According to the chemical composition of this capsular polysaccharide, the bacterium *N. meningitidis* is serogrouped in A, B, C, 29-E, H, I, K, L, W-135, X, Y or Z, and the major percentage of illness is caused by A, C, Y, W-135 and B. Non-encapsulated strains are not associated with the invasive disease.

Using different methods of purification of these polysaccharides (E. Gotschlich et al., 1969, J. Exp. Med. 129: 1349-1365) the four first polysaccharides (PS) showed to be good immunogens and inducers of bactericidal antibodies in humans (E. Gotschlich et al., 1969, J. Exp. Med. 129: 1367-1384). The presence of this kind of antibodies has been correlated previously with non-susceptibility to the infection (I. Goldschneider et al., 1969, J. Exp. Med. 129: 1307-1326). As of today mono-, bi- or tetravalent vaccines have been well studied for serotypes A, C and W-135 (F. Ambrosch et al., 1983, Bulletin of the WHO 61: 317-323; I. Vodopija et al., 1983, Infect. Immunol. 42: 599-604; M. Cadoz et al., 1985, Vaccine 3: 340-342; H. Peltola et al., 1985, Pediatrics 76: 91-96).

These vaccines have been licensed for their use in humans in different countries (Centers for Disease Control, 1985, Morbid Mortal. Weekly Report 34: 255-259) and some of them are commercially available from different firms and producers (Connaught Laboratories, USA; Smith Kline-RIT, Belgium; Institute Merieux, France; Behringwerke Aktiengesellschaft, Germany; Istituto Sieroterapico e Vaccino genea Toscano "Sclavo", Italy; Swiss Serum and Vaccine Institute, Berne, Switzerland; among others).

However, the conventional vaccine against *N. meningitidis* serogroup C does not induce sufficient levels of bactericidal antibodies in children under 2 years old, which are the principal victims of this disease. It has been demonstrated that the titer of specific antibodies against *N. meningitidis* in children under four years of age, after three years of vaccination, is similar in vaccinated and in non-vaccinated ones (H. Kayhty et al., 1980, J. of Infect. Dis. 142: 861-868). Also, no memory response was found against *N. meningitidis* after 8 years of vaccination in young adults (*N. Rautonen* et al., 1986, J. of Immunol. 137: 2670-2675).

The polysaccharide corresponding to *N. meningitidis* serogroup B is poorly immunogenic (E. Gotschlich et al., 1969, J. Exp. Med. 129: 1349-1365) and induces a poor response of IgM of low specificity (W. Zollinger et al., 1979, J. Clin. Invest. 63: 836-848). There are different theories related to this problem, such as cross-reactivity between B polysaccharide and fetal brain structures, antigenic structures modified in solution and sensitivity to neuroaminidases (C. Moreno et al., 1985, Infect. Immun. 47: 527-533). Recently, a chemical modification of PS B was achieved, which induced a response in the host (H. Jennings et al., 1988, U.S. Pat. No. 4 727 136; F. Ashton et al., 1989, Microb. Pathogen. 6: 455-458), but safety of this vaccine in humans has not been demonstrated.

Due to the lack of an effective vaccine against *N. meningitidis B*, and because the risk of endemic infection is low and mainly restricted to children, a routine immunization with polysaccharides is not recommended (C. Frasch, 1989, Clin. Microbiol. Revs. 2: S134-S138) except in the case of an epidemic.

Since after the Second World War the disease was caused in most of the cases by *N. meningitidis* B, vaccines against serogroup B gained special significance.

Other outer membrane components of *N. meningitidis* include phospholipids, lipopolysaccharides (LPS or endotoxins), pili proteins and others. Different immunotypes of LPS have been described for *N. meningitidis* (W. Zollinger and R. Mandrell, 1977, Infect. Immun. 18: 424-433; C.M. Tsai et al., 1983, J. Bacteriol. 155: 498-504) and immunogenicity using non-toxic derivatives was assayed (H. Jennings et al., 1984, Infect. Immun. 43: 407-412) but their variability (H. Schneider et al., 1984, Infect. Immun. 45: 544-549) and pyrogenicity (when it is conjugated to lipid A) are limiting factors up to now.

The pili, structures needed to fix cells to nasopharingeal mucous membrane (D. Stephens et al., 1983, The J. Infect. Dis. 148: 369-376) have antigenic diversity among different strains (J. Greenblatt et al., 1988, Infect. Immun. 56: 2356-2362) with some common epitopes (D. Stephens et al., 1988, The J. Infect. Dis. 158: 332-342). Presently there are some doubts in relation to the effectiveness of a vaccine based on these structures. However some of these types of vaccine have been obtained, without known results related to their use in humans (C. Brinton, 1988, U.S. Pat. No. 4,769,240).

Recently, the attention has switched to the other proteins of the outer membrane of this bacterium. There are many immunological types of these protein complexes.

The strains of *N. meningitidis* are subdivided in serotypes according to the presence of specific epitopes in the majoritary protein P1/P2 and in subtypes according to other epitopes in protein P1 (C. Frasch et al., 1985, Rev. Infect. Dis. 7: 504-510).

There are several published articles and patent applications concerning vaccines based on cocktails of these proteins, with previous selective removal of endotoxins using biocompatible detergents. The immunogenicity of these cocktails in animals and humans has been demonstrated (W. Zollinger et al., 1979, J. Clin. Invest. 63: 836-848; C. Frasch and M. Peppler, 1982, Infect.

Immun. 37: 271-280; E. Beuvery et al., 1983, Infect. Immun. 40: 369-380; E. Rosenqvist et al., 1983, NIPH Annals 6: 139-149; L. Wang and C. Frasch, 1984, Infect. Immun. 46: 408-414; C. Moreno et al., 1985, Infect. Immun. 47: 527-533; E. Wedege and L. Froholm, 1986, Infect. Immun. 51: 571-578; C. Frasch et al., 1988, The J. Infect. Dis. 158: 710-718; M. Lifely. and Z. Wang, 1988, Infect. Immun. 56: 3221-3227; J. Poolman et al., 1988, In J. Poolman et al (Eds), Gonococci and Meningococci, Kluwer Academic Publishers, Dordrecht, The Netherlands, pp 159-165; E. Rosenqvist et al., 1988, J. Clin. Microbiol. 26: 1543-1548), including results in massive field trials e.g. Capetown, South Africa in 1981 (C. Frasch, 1985, Eur. J. Clin. Microbiol. 4: 533-536); Iquique, Chile, 1987 (W. Zollinger, 1988, Proceedings of the Sixth International Pathogenic Neisseria Conference. Callaway Gardens Conference Center) and Cuba 1986 and 1988 (G. Sierra, 1988, Proceedings of the Sixth International Pathogenic Neisseria Conference. Callaway Gardens Conference Center). However, with the exception of the last case, the bactericidal antibodies induced by these preparations were restricted to the same serotype strains or related ones.

One of these vaccines is referred to in U.S. Pat. No. 4,601,903 which is restricted to one of the Neisseria types producing meningitis (serotype 2), with a high incidence, but also other serotypes have been isolated with high frequency from patients, such as serotypes 4 (Cuba from 1981 to 1983, H. Abdillahi et al., 1988, Eur. J. Clin. Microbiol. Infect. Dis. 7:293-296; Finland from 1976 to 1987, H. Kayhty et al., 1989, Scand. J. Infect. Dis. 21: 527-535); 8 (Australia from 1971 to 1980, F. Ashton et al., 1984, Can. J. Med. Biol. 30: 1289-1291) and 15 (Norway from 1982 to 1984, L. Froholm et al., 1985, Proceedings of the Fourth International Symposium on Pathogenic Neisseria. American Society for Microbiology; Chile from 1985 to 1987, S. Ruiz et al., 1988, Proceedings of the Sixth International Pathogenic Neisseria Conference. Callaway Gardens Conference Center) as well as strains of undefined serotype (F. Ashton et al.,1980, Can. J. Microbiol. 26: 1480-1488; Australia from 1971 to 1980, F. Ashton et al., 1984, Can. J. Med. Biol. 30: 1289-1291; Finland from 1976 to 1987, H. Kayhty et al., 1989, Scan. J. Infect. Dis. 21: 527-535).

The Cuban vaccine achieved in 1988 by the Centro Nacional de Biopreparados (European Patent Application. No. 301 992) has proven to be very effective. It is based on a high molecular weight antigenic complex. It possesses a broad range of cross-reactivity with other strains and produces and maintains bactericidal antibodies in the immunized host.

However, the methods employed to obtain this type of vaccine start with the multiplication in an appropriate culture of a microorganism which is highly pathogenic, with the associated biological risk of handling directly the bacteria. Moreover, this kind of preparation contains lipopolysaccharides, a contaminant that, although it may increase the product's effectiveness, shows at the same time undesirable secondary effects because of its powerful pyrogenicity. Also, its variation in minor antigenic components, which form part of the preparation, cannot be controlled in the different batches, which makes it difficult to follow important parameters related to the reactogenicity and immunogenicity.

For this reason, there is increasing interest in the identification of nucleotide sequences coding for highly conserved proteins in all strains, and even more so the identification of inducer proteins of bactericidal antibodies common to the majority of pathogenic Neisseria, in order to obtain vaccine preparations with a broad spectrum of protection.

There are different proteins with high molecular weight which are present in low amounts in the outer membrane of $N.$ $meningitidis$ when this microorganism is grown in conventional culture media but have a strong response in affected individuals (J. Black et al., 1986, Infect. Immun. 54: 710-713; L. Aoun et al., 1988, Ann. Inst. Pasteur/ Microbiol. 39: 203-212) and/or increase their response under special culture conditions (J. van Putten et al., 1987, Antoine van Leeuwenhoek 53: 557-5564; A. Schryvers and L. Morris, 1988, Molecular Microbiol. 2: 281-288 and Infect. Immun. 56: 1144-1149). Some of these proteins are highly conserved among the different strains, in particular those related to the acquisition of iron by the microorganism, that have become interesting vaccine candidates (L. Mocca et al., 1988, Proceedings of the Sixth International Pathogenic Neisseria Conference. Callaway Gardens Conference Center; C. Frasch, 1989, Clin. Microbiol. Revs. 2: S134-S138).

In addition to pure proteins obtained from the microorganism or strains of related species (e.g. 37 kD protein, T. Mietzner and S. Morse, 1987, U.S. Pat. No. 4,681,761), several related genes have been cloned and expressed. Among these proteins are the following:

protease IgAl (J. Koomey and S. Falkow, 1984, Infect. Immun. 43: 101-107);

protein Pl (A. Barlow et al., 1987, Infect. Immun. 55: 2734-2740, and 1989, Molec. Microbiol. 3: 131-139);

protein P5a (T. Kawula et al., 1988, Infect. Immun. 56: 380-386);

protein P5c (T. Olyhoek and M. Achtman, 1988, Proceedings of the Sixth International Pathogenic N. Conference. Callaway Gardens Conference Center);

protein P4 (K. Klugman et al., 1989, Infect. Immun. 57: 2066-2071);

protein P2 (K. Murakami et al., 1989, Infect. Immun. 57: 2318-2323);

and from $N.$ $gonorrhoeae,$ which code for proteins with cross-reactivity with their corresponding proteins from $N.$ $meningitidis:$ antigen H.8 (W. Black and J. G. Cannon, 1985, Infect. Immun. 47: 322-325);

macromolecular complex (W. Tsai and C. Wilde, 1988, Proceedings of the Sixth International Pathogenic Neisseria Conference. Callaway Gardens Conference Center);

37 kDa protein, repressed in the presence of iron (S. Berish et al., 1988, Proceedings of the Sixth International Pathogenic Neisseria Conference. Callaway Gardens Conference Center).

The use of these proteins as active vaccine preparation has not been reported or the bactericidal tests of antibodies induced against them were negative, such as in the case of mouse monoclonal antibodies against H.8 (J. Woods et al., 1987, Infect. Immun. 55: 1927-1928).

Up to the moment, the protein P1 located in the outer membrane of $N.$ $meningitidis$ is one of the best characterized and studied antigens. This protein presents no variability within the same strain. However, there are more than 17 types of proteins P1 in Neisseria which have differences in three variable regions, this being the basis of the classification of N. in different subtypes. This protein is very immunogenic in humans (W. D. Zollinger and R. E. Mandrell, 1983, Med. Trop. 43:143-147), eliciting protective antibodies (E.

Wedege and L. O. Froholm, 1986, Infect. Immun. 51: 571-578; K. Saukkonen et al, 1987, Microb. Pathogen. 3:261-267), that give it a special importance in vaccine preparations.

Some subtypes of proteins Pl have been cloned in *E. coli*, starting from genomic libraries (A. K. Barlow et al., 1989, Molec. Microb. 3:131-139) or using the PCR technique (S. Butcher et al., VIIth International Congress of Neisseria, R. C. Seid, Patent Application WO 90/06696; Brian Mc Guinness et al., 1990, J. Exp. Med. 171:1871-1882, M. C. J. Maiden et al., VIIth International Conference of Neisseria, Berlin, Sept. 9-14, 1990, and 1991, Molec. Microb. 3:727; J. Suker et al., VIIth International Conference of Neisseria, Berlin, Sept. 9-14, 1990). However, up to now, there is no genetic construction able to produce this protein with high levels of expression. Only low levels of expression (D. A. White et al., 1990, Molec. Microb. 4:769:776) or its expression in *Bacillus subtilis* fused to the outer membrane protein A of *E. coli* (omp A) (E. Wahlstrom et al., VIIth International Congress of Neisseria, September 9-14, 1990, Berlin) have been reported.

It can be affirmed that up to the moment no antigen has been isolated which is common to all types and serogroups of *N. meningitidis* and is able to produce bactericidal antibodies. For this reason, an antigen of this kind, conjugated or fused to other proteins or polysaccharides of immunological interest, would be relevant as a candidate for bivalent vaccine preparations.

This invention is related to a nucleotide sequence coding for a protein having a molecular weight of about 64 kilodaltons. This sequence has been found in all *N. meningitidis* serotypes and serogroups tested, as verified by nucleic acid hybridization, Western-bloting, Dot-blot and ELISA.

A technical object of this invention is the identification of a nucleotide sequence which codes for a highly conserved protein and is common to the majority of pathogenic strains of Neisseria (named P64k), in order to obtain the protein by a recombinant way with a high grade of purity and in commercially useful quantities, so that it can be employed in diagnostic methods and as an integrating part of a vaccine preparation of broad spectrum of protection.

On the level of genetic information (DNA and RNA), the invention provides a recombinant polynucleotide, comprising a nucleotide sequence coding for a protein P64k of *Neisseria meningitidis*, said protein P64k essentially having the amino acid sequence shown in SEQ ID NO:1. In a preferred embodiment said nucleotide sequence coding for the protein P64k of *N. meningitidis* essentially consists of the nucleotide sequence shown in SEQ ID NO:1. The recombinant polynucleotide may further comprise a nucleotide sequence of a cloning or expression vector.

The invention also provides a transformed microorganism containing a recombinant polynucleotide as defined above, preferably a transformed microorganism which is capable of expressing the protein P64k of *N. meningitidis*. In a particularly preferred embodiment of the invention, the transformed microorganism is an *Escherichia coli* strain, e.g. *E. coli* strain HB101, transformed with an expression vector containing a nucleotide sequence coding for the protein P64k of *N. meningitidis*, e.g. the expression vector pM-6.

The invention also provides a recombinant proteinaceous substance, comprising an amino acid sequence corresponding to the amino acid sequence of at least a part of a protein P64k of *N. meningitidis*, said protein P64k essentially having the amino acid sequence shown in SEQ ID NO:1. Said recombinant proteinaceous substance may essentially consist of protein P64k, or be a fusion protein or a protein/polysaccharide conjugate comprising the amino acid sequence of protein P64k of *N. meningitidis*.

The invention further provides a vaccine composition, comprising a recombinant protein as defined above, together with a suitable carrier, diluent or adjuvant. A particular embodiment of this invention provides a vaccine composition, comprising a lipoamide dehydrogenase or acetyl transferase capable of inducing antibodies which can bind a protein P64k of *N. meningitidis*, together with a suitable carrier, diluent or adjuvant.

In addition, the invention provides a monoclonal antibody, raised against a recombinant proteinaceous substance as defined above, or against a lipoamide dehydrogenase or acetyl transferase, and capable of binding a protein P64k of *N. meningitidis*.

The invention also provides a process for preparing a protein P64k of *Neisseria meningitidis*, or a fusion protein comprising protein P64k, said protein P64k essentially having the amino acid sequence shown in SEQ ID NO:1, comprising the steps of transforming a microorganism with an expression vector containing a nucleotide sequence coding for said protein P64k, or said fusion protein, culturing the transformed microorganism to obtain expression of said protein P64k, or said fusion protein, and isolating said expression product.

One novel aspect of this invention is the gene isolated from the *N. meningitidis* strain B:4:P1.15, which was named M-6 and has as a principal characteristic its stability in *E. coli* vectors. This gene does not produce adverse effects on the host, allowing to obtain yields of over 25% of total protein (ratio of P64k to total protein from host strain). On the other hand, it has been demonstrated by Southern and Western Blot hybridizations (E. Southern, 1975, J. Mol. Biol. 98: 503–527 and W. Burnette, 1981, Anal. Biochem. 12: 195–203) that protein P64k is present in all the following studied strains of *N. meningitidis:*

*N. meningitidis* A
*N. meningitidis* B:1
*N. meningitidis* B:2
*N. meningitidis* B:4
*N. meningitidis* B:5
*N. meningitidis* B:8
*N. meningitidis* B:9
*N. meningitidis* B:11
*N. meningitidis* B:15
*N. meningitidis* B:4:P1.15
*N. meningitidis* C
*N. meningitidis* B:15:P1.16
*N. meningitidis* B:15:P1.16 (H 44/76)
*N. meningitidis* B:NT (121/85)
*N. meningitidis* B:NT (71/86)
*N. meningitidis* B:NT (210/86)

and also in *N. mucosa, N. subflava* and *N. gonorrhoeae*. The protein is not present in *N. cinerea, N. lactamica, N. sicca* and *N. flavescens*, but these are not of interest because they are not pathogenic.

The protein having a molecular weight of about 64 kDa can be localized by electron microscopy in the outer membrane of *N. meningitidis*. Therefore, this antigen is an exposed antigen which is favorable for use in a vaccine preparation. The protein was recognized in Western blot immunoidentification experiments with sera from convalescents and individuals vaccinated with the conventional Cuban vaccine Va-Mengoc-BC (Centro Nacional de Biopreparados, Havana, Cuba). This aspect guarantees the immunogenicity of the antigen and at the same time confirms its presence within the high molecular weight protein fraction constituent of this vaccine, which is responsible of the lasting immune response to the disease.

Another novel aspect is that the protein, which is an object of this invention, produces antibodies with a broad bactericidal spectrum (different serogroupes, serotypes and subtypes), a characteristic which has not been reported previously for any protein from *N. meningitidis*.

This protein obtained in high levels in *E. coli* becomes an important candidate for the improvement of immunogenicity when expressed as a fusion protein with other proteins. It could also increase the expression by conferring enhanced stability and suitability in the molecular structure during transcription and translation processes. Belonging to Neisseria, this protein can also be fused to other proteins from Neisseria in order to obtain vaccine preparations against this microorganism with increased immunogenicity. These fusion proteins are also objects of this invention.

On the other hand, surprisingly, it was found that the gene M-6 obtained from a genomic library of the strain *N. meningitidis* B:4:P1.15 showed a great homology with sequences of lipoamide-dehydrogenases and acetyl-transferases from other microorganisms and higher organisms. The presence of common antigenic determinants allows the use of these other related proteins as immunogens, able to confer protection by the induction of bactericidal antibodies which recognize the antigenic determinants common to protein P64k. Therefore, the use of these lipoamide-dehydrogenases and acetyl-transferases (not isolated from *N. meningitidis*) or derivatives therefrom such as peptides, fragments from enzymatic degradation, constructions of fusion with other proteins, or conjugation with proteins, polysaccharides or lipids, or insertion in complexes as liposomes or vesicles, etc., for vaccine purposes, are included in the scope of this invention.

An important object of this invention is the nucleotide sequence which codes for the M-6 gene (SEQ ID NO:1 of the Sequence Listing) whose product is the protein P64k. This gene was derived from the genome of the strain B385 isolated in Cuba (*N. meningitidis* B:4:P1.15), by the construction of a genomic library in the phage EMBL 3.

The recombinant DNA including the gene M-6 constitutes another object of this invention, which includes the phage lambda, the plasmid pM-3 and the expression vector pM-6 for expression in bacteria.

In particular, for the intracellular expression in *E. coli*, the M-6 gene was cloned under the tryptophane promoter and using its own termination signal of transcription and a linkage fragment between M-6 and the cloning site NcoI which adds the following nucleotide sequence at the 5' end:

ATG CTA GAT AAA AGA    (SEQ ID NO:2)

The N-terminal of the protein P64k encoded by the M-6 gene inserted in plasmid pM-6 which adds 5 aminoacids to the N-terminal of the original protein corresponds to:

(SEQ ID NO:3)
M L D K R M A L V E L K V P D I G G H E N V D I I

Another object of this invention are the microorganisms resulting from the transformation of *E. coli* strain HB 101 with the pM-6 vector, which are characterized by the expression of high levels of protein P64k, good viability and great stability.

The transformed clone of *E. coli* was denominated HBM64 (FIG. 2), and presents levels of expression of P64k higher than 25% in relation to the total protein of the cell (FIG. 6). The procedure described in the present invention, due to the levels of expression achieved for this product, allows to reach an optimal purity for use of this protein in humans.

On the other hand, the antigen obtained from the isolated sequence was very useful in the preparation of different types of potential vaccine preparations, like bivalent vaccines with a broad immunoprotective spectrum, e.g., protein-polysaccharide conjugates, fusion proteins, etc.

BRIEF DESCRIPTION OF THE DRAWINGS

The drawings presented herein may be described briefly as follows.

EXAMPLES

These examples intend to illustrate the invention, but not to limit the scope of this invention.

EXAMPLE 1

For the isolation of genomic DNA from *N. meningitidis* B:4:P1.15, the cells were grown in Mueller-Hinton medium (OXOID, London). The biomass from a culture of 100 ml was resuspended in 8 ml of Tris (hydroxymethyl-aminomethane) 00 mM, EDTA (ethylenediamine tetraacetic acid) lmM, pH 8. The cells were subjected to a treatment with lysozyme (10 mg/ml), followed by 200 μl of self-digested pronase (20 mg/ml) and 1.1 ml of 10% SDS. The mixture was incubated at 37° C. during 1 hour, then it was treated with phenol-chloroform (v/v) and the remains of phenol were eliminated using 2-butanol. Finally, the DNA was precipitated with absolute ethanol and RNA was eliminated with ribonuclease A (Sigma, London).

The DNA of about 60 kb was subjected to a partial digestion with the enzyme Sau 3A, obtaining a population of fragments of about 15 kb. This majoritary fraction was isolated and purified by separation in agarose gel (T. Maniatis et al., 1982, Molecular Cloning: A Laboratory Manual. Cold Spring Harbor Lab.: Cold Spring Harbor N.Y.).

For the construction of the genomic library, the process described by Maniatis was essentially followed (T. Maniatis et al., 1982, Molecular Cloning: A Laboratory Manual. Cold Spring Harbor Lab.: Cold Spring Harbor N.Y.). Four μg of purified DNA were ligated with 8 μg of BamHI-digested EMBL-3. The ligation product was packed and the phages were finally plated on the *E. coli* strain C66P2.

The library was screened by immunoidentification (R. Young and R. Davis, 1983, PNAS USA 80: 1194-1198) using rabbit serum obtained against a preparation of proteins belonging to the outer membrane of the strain *N. meningitidis* B:4:P1.15. The clones were analyzed by Western-blot (Burnette, 1981) and the expression of the P64k protein with a molecular weight of about 70 kDa was detected. The resulting recombinant phage was named 31. The Western blot was also made using a mixture of sera from convalescents of meningococcemia, free of antibodies from *E. coli*, obtaining the same result as that using hyperimmunized rabbit sera.

This experiment was repeated using sera from several healthy individuals, and the signal obtained was negative against the recombinant protein P64k.

EXAMPLE 2

For subcloning in bacteria, the 17 kb insert corresponding to the phage isolated from the library was cloned in the plasmid pUC18 after separation from the phage's arms using the enzyme SalI. This resulted in the construction pM-1 (FIG. 2), that was subjected to restriction analysis (FIG. 3).

Figure 2:
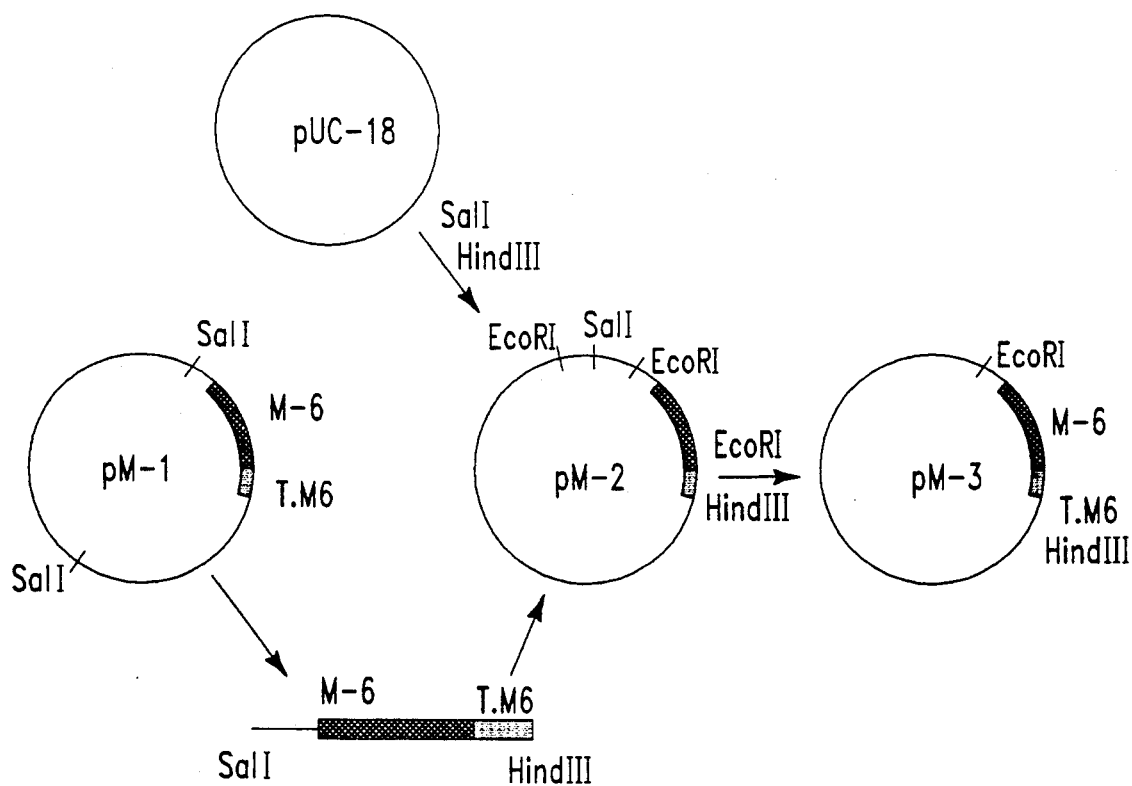
FIG. 2 is a schematic representation of the transformed clone of *E. coli*.
Figure 3:
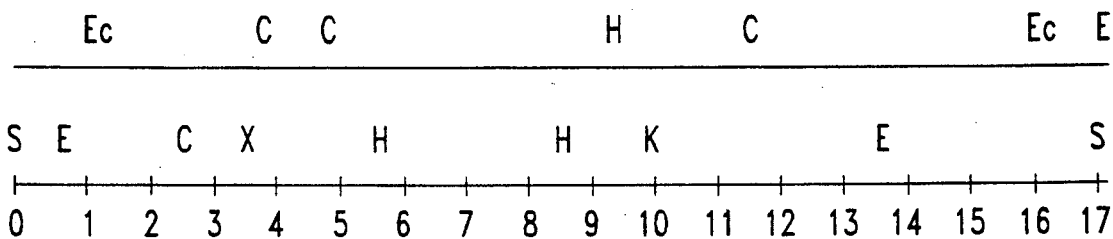
FIG. 3 shows the results when the pM-1 construction is subject to restriction analysis.

The fragment SalI-HindIII of about 6 kb was recloned in the plasmid pUC18 and the construction pM-2 was obtained (FIG. 2). In order to obtain a more exact localization of the gene coding for protein P64k deletions were carried out with the enzymes ClaI, EcoRI and HincII. The complete fragment of the gene M-6 was finally localized as an EcoRI-HindIII insert corresponding to the construction pM-3 (FIG. 2).

In all constructions, the presence of the gene was confirmed by recognizing the protein by colony immunoidentification and Western Blot using hyperimmunized rabbit sera.

The sequence of the insert in pM-3 was determined by the method of Sanger (F. Sanger et al., 1977, PNAS USA 74: 5463-5467).

From the obtained sequence, the approximate molecular weight of the protein encoded by the gene was deduced.

In order to obtain a construction for high expression of the protein P64k, the plasmid pM-3 (FIG. 2) was linearized with the enzyme EcoRI and successive suppressions of the gene were carried out, incubating the sample with the nucleases ExoIII and S1.

The resulting fragments were separated from the rest of the vector pUC18 by cutting with the restriction enzyme HindIII and were cloned fused to a stabilizator fragment (European patent application EP-A-0 416 673), using an Xba-blunt adapter to conserve the XbaI site of the stabilizator gene:

5' C T A G A T A A A A G A 3'    SEQ ID NO:4)

3'            T A T T T T C T  5'    SEQ ID NO:5)

The constructions in which the fused fragment coincided with the reading frame were selected by immunoidentification using hyperimmune rabbit sera.

The insert sequences were established using Sanger's Method (F. Sanger et al., 1977, PNAS USA 74: 5463-5467). From the obtained sequences the approximate molecular weight of the protein encoded by this gene was deduced.

Figure 4:
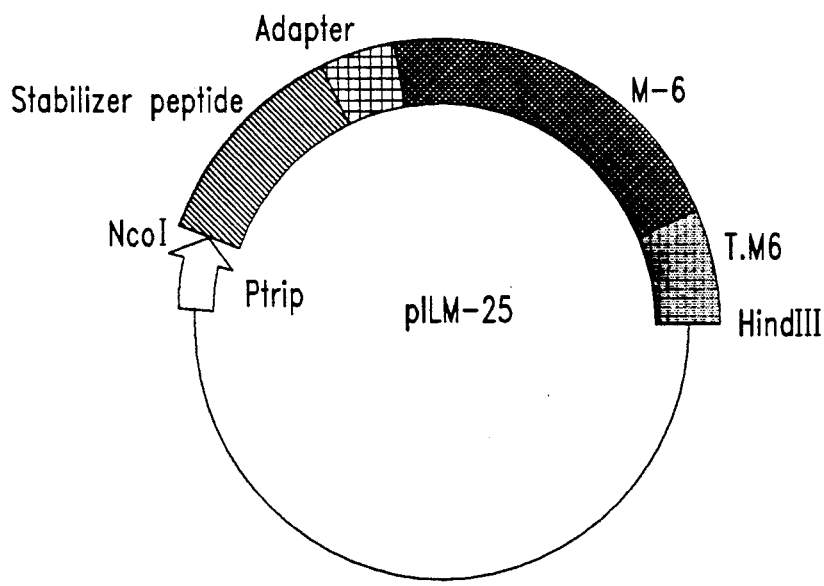
FIG. 4 is a representation of the clone pILM-25.

The fusion region between the proteins was localized in the gene sequences. In the clone pILM-25 (FIG. 4) the ATG of the gene predetermined by the sequence of the DNA insert isolated from the library, coincided with the fusion site.

Figure 1:
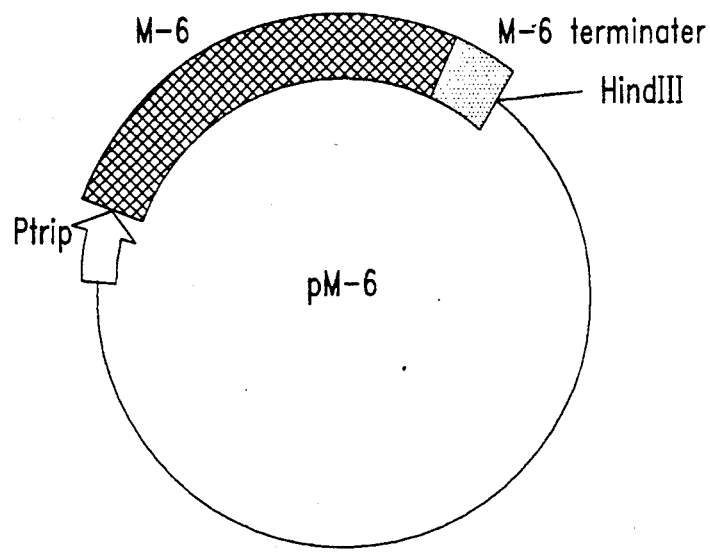
FIG. 1 represents the plasmid (pM-6) construction

The NcoI-XbaI fragment, corresponding to the stabilizing peptide coding sequence, was deleted from pILM-25, obtaining a non-fused protein expressed under the tryptophan promoter with it's original terminator from the *N. Meningitidis* B:4:P1.15, according to the pM-6 construction (FIG. 1).

The pM-6 plasmid was transformed in different strains of *E. coli* like W3110, JA-221, HB-101, LE-392 and MC-1061, and the expression of P64k was compared. The best results were obtained in W3110, JA-221 and HB-101. These strains were chosen to scale up fermentation, and expression levels up to 25% of total cell proteins were obtained.

EXAMPLE 3

To confirm the correct expression of the cloned gene the N-terminal region of the intact protein was subjected to the Edman degradation method (P. Edman, 1950, Acta Chem. Scand. 4: 283-293). This technique elucidates the sequence (primary structure) of this region in the molecule.

The P64k protein was desalted by gel filtration chromatography (PD-10, Pharmacia), eluted with water and monitored at 280 nm. The protein fraction was concentrated to 0.5 nM/μl. One μl of this solution was applied to a PVDF (polyvinylidene difluoride, Millipore) filter, previously activated with methanol.

The Edman degradation was made using the Knauer's Automatic Sequencer, model 810, connected to a HPLC (High Performance Liquid Chromatography) system, so as to detect the phenylthiohydantoin derivatives of the aminoacids (PTH-aminoacids). The standard procedure of sequencing as recommended by the manufacturer of the equipment was followed. The separation of the PTH-aminoacids was performed in a reverse phase column C-18 (5 μm), 250 mm×2 mm (Merck), eluted with an acetonitrile gradient (B buffer) in sodium acetate (A buffer), prepared according to the manufacturers, with a 200 μl/minute flow and at 42° C. The PTH-aminoacids were detected at 269 nm.

Data processing and registration were made in a Shimadzu model CR-6a automatic integrator, using a program for data processing by subtraction of two consecutive chromatograms, to facilitate the evaluation of the Edman degradation cycles. Sequence identification is obtained by the chromatographic evaluation of the corresponding analyzed cycle and confirmed by the chromatogram obtained by subtraction, allowing to determine 25 residues.

EXAMPLE 4

To demonstrate that the protein P64k is recognized by the sera of individuals vaccinated with the Cuban Va-Mengoc-BC preparation (Centro Nacional de Biopreparados, Havana, Cuba.), a Western-Blot was made, with a mixture of 12 sera from adults (immunized with two doses of the Cuban vaccine) diluted in a solution containing defatted milk (Oxoid, London). The experiment included:

recombinant protein P64k, purified from *E. coli* HB-101 transformed with the pM-6 plasmid;

supernatant of the ultrasonic cell rupture of untransformed *E. coli* HB-101;

the reaction was revealed with a protein A-colloidal gold conjugate.

It was shown that the protein P64k is recognized by the pool of sera.

EXAMPLE 5

The bactericidal test against B385 (B:4:P1.15) was made according to the procedure described by Larrick et al. (Scand. J. Immunol. 32, 1990, 121–128) with modifications. With this objective, a mixture was made of a) a suspension of bacteria, cultured under special conditions (1–5 colony forming units/l), b) Gey's balanced salt solution, c) rabbit sera (3 to 4 weeks) as a source of complement and d) pooled sera from mice, immunized against protein P64k in Aluminium Hydroxyde Gel, and inactivated at 56° C. for 30 minutes. The immunization of mice was carried out according to an immunization scheme of 3 doses of 20 μg each. The proportions used in the aforementioned mixture were 1:2:1:1 in a total volume of 125 μl. The mixture was incubated at 37° C. during 1 hour and plated in fresh Mueller Hinton Agar (Oxoid, London) supplemented with 5% calf serum (CubaVet, Habana). The counting of surviving colonies was done after 18 hours of incubation of the plates in an atmosphere of 5% $CO_2$ at 37° C.

The bactericidal titer was considered as the maximum serum dilution necessary to render a 50% inhibition of bacterial growth, with respect to the same mixture without the test serum. It was found that 1:20 serum dilution still maintains its bactericidal activity. As negative controls (non bactericidal at 1:2 dilution) pooled sera from mice immunized with Aluminum Hydroxyde Gel, and pooled sera from mice immunized with cuban Hepatitis B recombinant vaccine, were used. The bactericidal effect was specific to the anti-P64k antibodies.

EXAMPLE 6

The bactericidal test against different strains of *N. meningitidis* was made using:

1. An ammonium sulphate precipitate of the supernatant harvested from a culture of hybridoma cells secreting monoclonal antibodies specific against P64k (anti P64k)/Sample to analyze.

2. An ammonium sulphate precipitate of the supernatant harvested from hybridoma cells secreting monoclonal antibodies specific against the P1.15 protein present in *N. meningitidis* strain B385 (anti P1.15)/Positive control of the system.

The maximum dilutions tested were always 1:16. The maximum dilutions tested which had a bactericidal effect, according to the EXAMPLE 5, are indicated:

| Strain | anti-P64k | anti-P1.15 |
| --- | --- | --- |
| B385 | 1:16 | 1:16 |
| B:4:P1.15 | 1:16 | 1:16 |
| B:14:P1.7 | 1:16 | — |
| B:NT:NT | 1:16 | — |
| B:15:P1.15 | 1:8 | — |
| B:15:P1.16 | 1:8 | — |
| B:13 | 1:8 | — |
| C | 1:16 | — |
| A | 1:16 | — |

As seen, the anti-P64k monoclonal antibodies have significant bactericidal titers against different serogroups (A, B and C), serotypes (4, 14, 13, 15 and NT) and subtypes (7, 15, 16 and NT) of bacteria.

EXAMPLE 7

Fusion protein M-14 (P64k and P1.15)

In order to obtain a genetic construction for high expression that contained the variable epitopes of the P1.15 protein (Outer membrane protein from *N. meninigitidis* B:4:P1.15) fused to the P64k protein, the gene coding for P1.15 protein was cloned using the Polymerase Chain Reaction (PCR). The following region containing the variable immunodeterminants of P1.15:

```
L Q L T E P P S K S Q P Q V K V T K A K S R I R T K I S D F G   (SEQ ID NO:6)

S F I G F K G S E D L G E G L K A V W Q L E Q D V S V A G G G

A T Q W G N R E S F V G L A G E F G T L R A G R V A N Q F D D

A S Q A I D P W D S N N D V A S Q L G I F K R H D D M P V S V

R Y D S P D F S G F S G S V Q F V P I Q N S K S A Y T P A Y H

Y T R Q N N A D V F V P A V V G K P G S D V Y V A G L N Y K N

G G F A G S Y A F K Y A R H A N V G R N A F E L F L L G S T S

D E A
``` was inserted in the Mlu I site of the gene M-6, encoding for P64k, after having been made blunt with the klenow fragment from DNA polymerase I. The sites for gene fusion of P1.15 with M-6 are the following:

GDALQL  (SEQ ID NO:7)

| Gly | Asp | Ala | Leu | Gln | Leu | (SEQ ID NO:8) |
|---|---|---|---|---|---|---|
| 5'- GGC | GAC | GCG | CTG | CAG | TTGA -3' | |
| | | M-6 | | | P1.15 | |

EANAYE  (SEQ ID NO:9)

| Glu | Ala | Asn* | Ala | Tyr | Glu | (SEQ ID NO:10) |
|---|---|---|---|---|---|---|
| 5'- GAA | GCC | AAC | GCG | TAC | GAA -3' | |
| | P1.15 | | | | M-6 | |

*N does not belong to any of the fusion proteins and was created by the genetic construction.

The resulting fusion protein (M-14) was expressed in *E. coli* using a plasmid vector under the tryptophan promoter, to levels higher than 10% of total cell protein. The protein was recognized by bactericidal monoclonal antibodies, and anti-P1.15 and P64k polyclonal antibodies, in Western-Blot.

EXAMPLE 8

Polysaccharide/P64k conjugation.

The protein P64k was conjugated with the polysaccharide from *Haemophilus influenzae* using the reductive amination method. The *Haemophilus influenzae* polysaccharide (Polyribosyl ribitol phosphate, PRP) was purified by the cold phenol method described by Frasch, 1990 (in: Bacterial Vaccines, 1990, Alan R. Liss, Inc., pp. 123-145). The final contamination of PRP with proteins or nucleic acids was less than 1%. This polysaccharide was degraded using the method of Parikh et al. 1974 (Methods in Enzymol. 34B: 77-102) with sodium periodate in PRP (ratio 1:5 w/w) dissolved in 0.1M sodium acetate (pH 4.5). The incubation was carried out in the dark during 30 minutes with stirring. The periodate excess was eliminated by addition of ribitol. Very low molecular weight compounds were eliminated by dialysis (Medicell International Ltd. Membrane, London). The resulting oligosaccharide had free aldehyde groups able to react with primary amines (e.g. lysine residues in proteins). The conjugate is obtained by mixing protein and polyssacharide in a 1:1 ratio (w/w), adding sodium cyanoborohydride and subjecting the mixture to an incubation, first for 48 hours at 4° C. and later at 37° C. for 24 hours. The high molecular weight complex which contains the resulting conjugate with protein-polysaccharide in a 1:2.3 ratio, can be separated from the non reactive contaminants by HPLC.

EXAMPLE 9

Bivalent vaccine preparation against Hepatitis B virus and *N. meningitidis*.

In order to obtain a bivalent vaccine preparation, different quantities of protein P64k and Hepatitis B Surface Antigen (Vacuna Recombinante contra la Hepatitis B, Heber Biotec, Havana, Cuba) were mixed. The antigens were adjuvated with Aluminum Hydroxyde Gel, at 2 mg/dose and inoculated in Balb/c mice having a body weight of 20 g in 3 dosis of 0.5 ml each. Different variants were assayed:
1. P64k 20 μg (P20)
2. HBsAg 20 μg (H20)
3. P64k 10 μg + HBsAg 10 μg (P10:H10)
4. P64k 15 μg + HBsAg 5 μg (P15:H5)
5. Placebo (Al(OH)$_3$)

Figure 5:
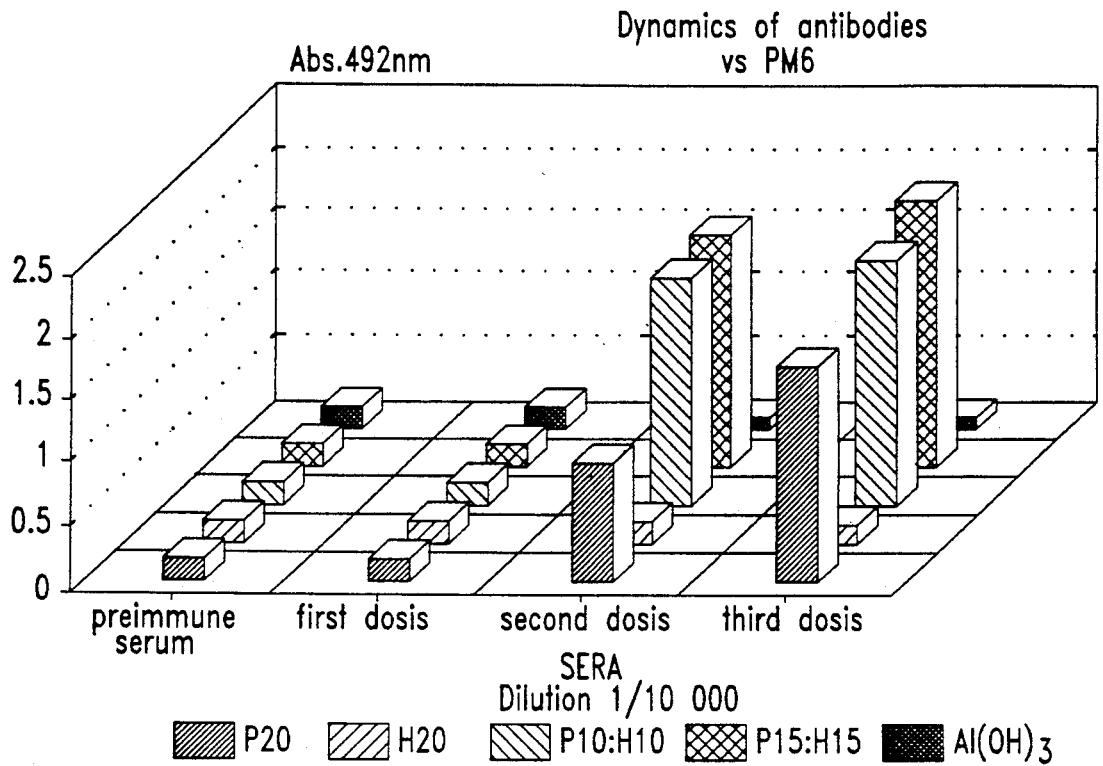
FIG. 5 is a graphical representation showing the dynamics of antibody response against protein p64K using sera diluted 1/10,000.
Figure 6:
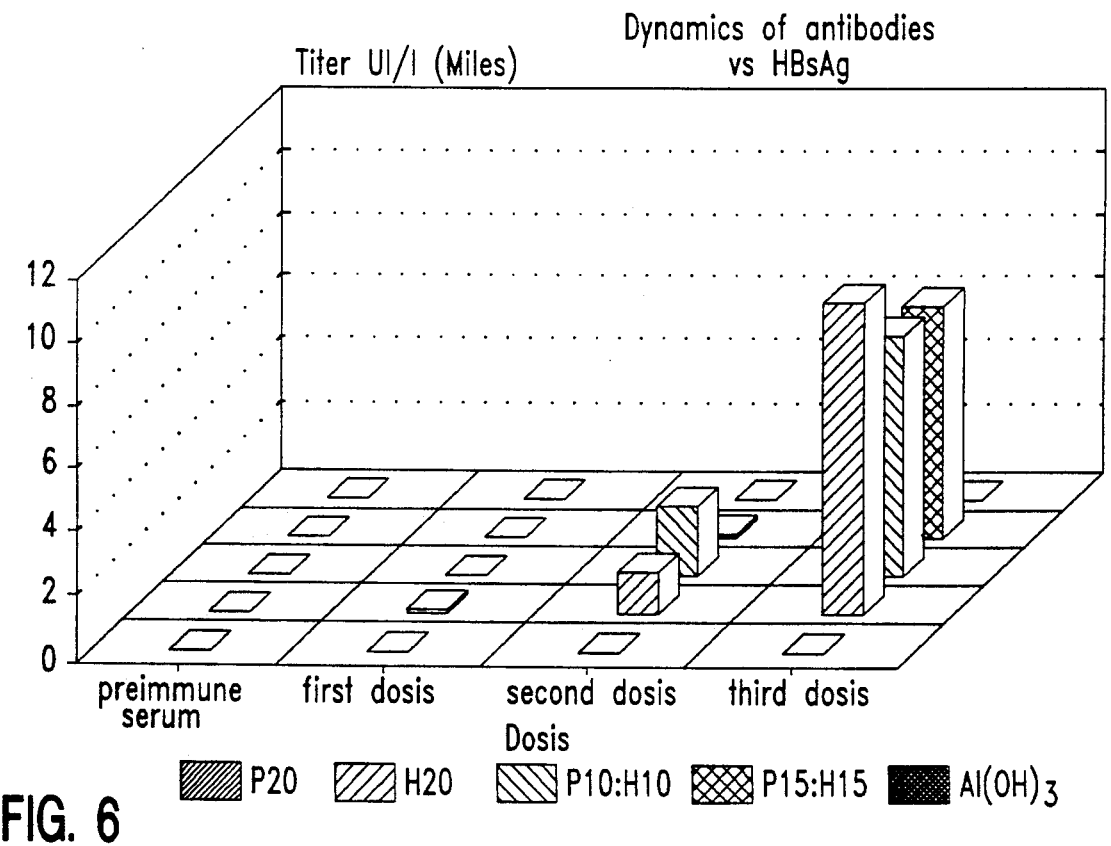
FIG. 6 is a graphical representation showing the titers against HBsAg after each dose of sera as shown in FIG. 5.

Seven days after the immunization with the first doses, the second doses were applied. The third dose was given 14 days after the second. Seven days later, blood was taken and the serum of each immunized animal was separated. Antibody titers against P64k protein were measured in solid phase Enzyme Linked Immunosorbent Assay (ELISA), using P64k at 5 mg/ml to coat the polystyrene plate. The antibody titers against HBsAg were determined by a Commercial ELISA (Organon Teknika, Boxtel). FIG. 5 shows the dynamics of antibody response against protein P64k, using sera diluted 1/10,000. The response against P64k is not interfered by the presence of the other antigen. FIG. 6 shows the titers against HBsAg after each dosis. The titers against this protein are not diminished by the presence of P64k in the preparation. High titers are obtained against both antigens in the same vaccine preparation.

EXAMPLE 10

A software was created to search the EMBL (European Molecular Biology Laboratoty) Data Base and detect the homology between P64k and other proteins. As result of the search it was found that there is homology of one segment in the sequence of P64k with segments in the sequences of *N. gonorrhoeae*. This sequence was found as characteristic in both *N. gonorrhoeae* and *N. meningitidis* (F. F. Correia, S. Inouye and M. Inouye, 1988, J. Biol. Chem. 263, No. 25, 12194-12198).

Another region with high homology was found in two proteins of the Pyruvate Dehydrogenase Complex from *E.coli* K12: a)Acetyltransferase from *E. coli* and the P64k outer membrane protein from *N. meningitidis*.

Homology exists between a segment comprising 100 amino acids, repeated at the beginning of the amino acid sequence of the Acetyltransferase ("Lipoyl Domain", including the "Lipoyl Binding Site" (P. E. Stephens et al., 1983,. Eur. J. Biochem. 133, 481-489)) and a region located in the first 111 amino acids of the P64k:

```
MAL V E L K V P D I  G G H E N V D I  I  A V E V N V G D T I  A V       (SEQ ID NO:11)
  _ * _  * * * * * *    _  * _ _    * *  * * *    _ *

V K E V N V P D I  G G   D E V E V T E V M V K V G D K V A A       (SEQ ID NO:12)

DDT L I  T L E T D K A T MD V P A E V A G V V K E V K V K V G         (SEQ ID NO:11) (cont)
_ _    * * * _ *   * * *   * _ * * *      * * * * * * _ * *   * *

E Q S L I  T V E G D K A S  M E V P A P F A G V V K E L K V N V G     (SEQ ID NO:12) (cont)

D K I  S E G G L I  V V V E A E G T — — A A A P K A E S A A — — A    (SEQ ID NO:11) (cont)
* * _     *  I * _ _   * * *       * * * *     _  * *     *

D K V K T G S L I  MI  F E V E G A A P A A A P A K Q E A A A P A      (SEQ ID NO:12) (cont)

P R K K P L K C R W V P Q A A Q F G G                                  (SEQ ID NO:11) (cont)
*   *         * *     *

P A A K A E A P A A A P A A K A E G K                                  (SEQ ID NO:12) (cont)
``` where (*) indicates positions with the same amino acids and (—) indicates positions of conservative amino acid changes.

b) Lipoamide Dehydrogenase from *E. coli* and Outer Membrane P64k protein from *N. meningitidis*.

Homology exists between the Lipoamide Dehydrogenase from *E. coli* (a protein having 473 amino acids, P. E. Stephens et al., 1983, Eur. J. Biochem. 133, 481-489) and the protein P64k, specifically in a segment which represents almost the total protein, except the region with homology with the "lipoyl domain" from Acetyltransferase.

```
            |----1----|
S A D A E Y D V V V L G G G P G G Y S A A F A A A D E G L K V A    (SEQ ID NO:13)
 *___ _ _*****_**_******   ** **___
S T E I K T Q V V V L G A G P A G Y S A A F R C A D L G L E T V    (SEQ ID NO:14)

|--------2---------|
I V E R Y K T L G G V C L N V G C I P S K A L L H N A A V I D E    (SEQ ID NO:13) (cont)
* * * * _* * * * * * * * * * * * * * * *  *  * * _*
I V E R Y N T L G G V C L N V G C I P S K A L L H V A K V I E E    (SEQ ID NO:14) (cont)

V R H L A A N G I K Y P E P A L D I D M L R A Y K D G V V S R L    (SEQ ID NO:13) (cont)
___ ** __** _ ** ***___*___*__ *_____*
A K A L A E H G I V F G E P K T D I D K I   T W K E K V I N Q L    (SEQ ID NO:14) (cont)

T G—F G R Y G E K R K V D V I Q G D G Q F L D P H H L E V S L      (SEQ ID NO:13) (cont)
** __  __  ***_*___* *_*  ___  *** _
T G G L A G M A K G R K V K V V N G L G K F T G A N T L E V E G    (SEQ ID NO:14) (cont)

T A G D A Y E Q A A P T G E K K I V A F K N C I I A A G S R V T    (SEQ ID NO:13) (cont)
___*           *_____*_* *******  _
E N G———————————————K T V I N F D N A I I A A G S R P I            (SEQ ID NO:14) (cont)

K L P F I P —E D P R I I D S S G A L A L K E V P G K L L I I G    (SEQ ID NO:13) (cont)
_***** ***** **___**_*****___**___*
Q L P F I P H E D P R I W D S T D A L E L K E V P E R L L V M G    (SEQ ID NO:14) (cont)

G G I I G L E M G T V Y S T L G S R L D V V E M M D G L M Q G A    (SEQ ID NO:13) (cont)
* * * * * * * * * * * _* * * ___* * * * * _*  _____*
G G I I G L E M G T V Y H A L G S Q I D V V E M F D Q V I P A A    (SEQ ID NO:14) (cont)

D R D L V K V W Q K Q N E Y R F D N I M V N T K T V A V E P K E    (SEQ ID NO:13) (cont)
*_*_***_ *__ _*__ _*___** ___***_**
D K D I V K V F T K R I S K K F N—L M L E T K V T A V E A K E     (SEQ ID NO:14) (cont)

D G V Y V T F E G A N P P K E P Q R Y D A V L V A A G R A P N G    (SEQ ID NO:13) (cont)
**_***_** ___* ***********  **_***
D G I Y V T M E G K K A P A E P Q R Y D A V L V A I G R V P N G    (SEQ ID NO:14) (cont)

K L I S A E K A G V A V T D R G F I E V D K Q M R T N V P H I Y    (SEQ ID NO:13) (cont)
* ___*_*****_*_***** ****_*********_
K N L D A G K A G V E V D D R G F I R V D K Q L R T N V P H I F    (SEQ ID NO:14) (cont)

A I G D I V G Q P M L A H K A V H E G H V A A E N C A G T K A Y    (SEQ ID NO:13) (cont)
* * * * * * * * * * * * * _* * * * * * * *   ** _*  *
A I G D I V G Q P M L A H K G V H E G H V A A E V I A G K K H Y    (SEQ ID NO:14) (cont)

F D A A V I P G V A Y T S P E V A W V G E T E L S A K R P A G K    (SEQ ID NO:13) (cont)
** _ *** ___***_*******  ** _**   __ __
F D P K V I P S I A Y T E P E V A W V G L T E K E A K E K G I S    (SEQ ID NO:14) (cont)

I T K A N F P W A A S G R A I A N G C D K P F T K L I F D A E T    (SEQ ID NO:13) (cont)
* _*************___*___ _****** *_
Y E T A T F P W A A S G R A I A S D C A D G M T K L I F D K E S    (SEQ ID NO:14) (cont)

G R I I G G G I V G P N G G D M I A K S A L P S K L G C D A A D    (SEQ ID NO:13) (cont)
* _***_***_*** _____ _*_ ___****_*
H R V I G G A I V G T N G G E L L G E I G L A I E M G C D A E D    (SEQ ID NO:14) (cont)

|__3_|
V G K T I H P R P T L G E S I G M A A E V A L G T C T D L P P Q    (SEQ ID NO:13) (cont)
___ ***___*** **_*_**** *__ **** _
I A L T I H A H P T L H E S V G L A A E V F E G S I T D L P N P    (SEQ ID NO:14) (cont)

——K K K      —     MENlpd                                          (SEQ ID NO:13) (cont)
 ***
K A K K K    —     EClpd                                           (SEQ ID NO:14) (cont)
```

Where:
|—1—|: Adenine binding site (FAD)
|—2—|: Redox active disulphide region
|—3—|: Active site histidine

Strain deposits

An *E. coli* HB-101 clone containing the plasmid pM-3 (a pUC18 plasmid containing the 4.1 kb DNA fragment from *Neisseria meninigitidis*, strain B:4;P1.15, cloned between the EcoRI and HindIII restriction sites), was deposited on Aug. 30, 1991, with the Centraalbureau voor Schimmelcultures (CBS), Oosterstraat 1, P.O. Box 273, 3740 AG Baarn, The Netherlands Baarn, The Netherlands, and obtained deposit number CBS 485 .91.

We claim:

1. A recombinant polynucleotide, comprising a nucleotide sequence coding for a protein P64k of *Neisseria meningitidis*, said protein P64k essentially having the amino acid sequence shown in SEQ ID NO:1.

2. A recombinant polynucleotide according to claim 1, wherein said nucleotide sequence coding for the protein P64k of *N. meningitidis* essentially consists of the nucleotide sequence shown in SEQ ID NO:1.

3. A recombinant polynucleotide as defined by claim 1, further comprising a nucleotide sequence of a cloning or expression vector.

4. A transformed microorganism, containing a recombinant polynucleotide claim 1.

5. A transformed microorganism according to claim 4, which is capable of expressing the protein P64k of *N. meningitidis.*

6. A transformed microorganism according to claim 5, which is an *Escherichia coli* strain, e.g. *E. coli* strain HB101, transformed with an expression vector containing a nucleotide sequence coding for the protein P64k of *N. meningitidis,* e.g. the expression vector pM-6.

7. An isolated and purified nucleotide sequence obtained by the isolation and expression of a gene which codes for a protein belonging to the outer membrane of *N. meningitidis* and its use in vaccine preparations wherein the gene from the strain of *N. meningitidis* B:4:P1.15, identified as M-6, is obtained from the screening of a genomic library in the EMBL 3, and is cloned and expressed in a suitable host, coding for protein of 64 kDa belonging to the outer membrane of *N. meningitidis* which has bactericidal activity against different serogroups, serotypes and subtypes of *N. meningitidis,* which includes a sequence corresponding with the M-6 gene and codes for the P64k protein identified by SEQ ID NO: 1.

8. A recombinant DNA claim 7, comprising the M-6 gene which codes for P64k protein.

9. A recombinant DNA according to claim 8, characterized comprising a phage, a plasmid and an expression vector.

10. A recombinant DNA as defined by claim 9, comprising phage EMBL 3, plasmid pM-1 and expression vector pM-6.

11. A transformed microorganism as defined by claim 4, which results from the transformation of a suitable host, carries the M-6 gene, expresses high levels of P64k protein and maintains good viability and cellular stability.

12. A transformed microorganism according to claim 11, which is the clone HBM64 which is obtained from the transformation of *E. coli* host strain HB101 with the expression vector pM-6, and it presents high stability and viability and expression levels of P64k protein higher than 25% of the total protein of the cell.

* * * * *

UNITED STATES PATENT AND TRADEMARK OFFICE
CERTIFICATE OF CORRECTION

PATENT NO.  : 5,286,484
DATED       : February 15, 1994
INVENTOR(S) : Rodriquez, et. al.

It is certified that error appears in the above-indentified patent and that said Letters Patent is hereby corrected as shown below:

Title page, item [54], and col. 1, line 3, after "FROM" remove the italics from the remaining of the title; and Title page, item [30],"Foreign Application Priority Data", delete "Jul. 9, 1990" and replace with --September 7, 1990--.

Signed and Sealed this

Ninth Day of August, 1994

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES:14

( 2 ) INFORMATION FOR SEQ ID NO: 1:

( i ) SEQUENCE CHARACTERISTICS:
( A ) LENGTH:1836 bp
( B ) TYPE:Nucleotide with corresponding amino acid
( C ) STRANDEDNESS: single
( D ) TOPOLOGY: linear ( i i ) MOLECULE TYPE: genomic DNA ( v i ) ORIGINAL SOURCE:
( A ) ORGANISM: N. meningitidis group B ( v i i ) IMMEDIATE SOURCE: Strain B:4:P1:15 isolated in Cuba ( i x ) FEATURE: From 1 to 1830 bp mature protein
( D ) OTHER INFORMATION:
Properties: Gene coding for P64k protein from outer membrane of N. meningitidis ( x i ) SEQUENCE DESCRIPTION: SEQ ID NO:1:

```
ATG CTA GAT AAA AGA ATG GCT TTA GTT GAA TTG AAA GTG CCC     42
Met Leu Asp Lys Arg Met Ala Leu Val Glu Leu Lys Val Pro
 1               5                  10

GAC ATT GGC GGA CAC GAA AAT GTA GAT ATT ATC GCG GTT GAA     84
Asp Ile Gly Gly His Glu Asn Val Asp Ile Ile Ala Val Glu
 15                  20                  25

GTA AAC GTG GGC GAC ACT ATT GCT GTG GAC GAT ACC CTG ATT    126
Val Asn Val Gly Asp Thr Ile Ala Val Asp Asp Thr Leu Ile
     30                  35                  40

ACT TTG GAA ACC GAT AAA GCG ACT ATG GAC GTA CCT GCT GAA    168
Thr Leu Glu Thr Asp Lys Ala Thr Met Asp Val Pro Ala Glu
         45                  50                  55

GTT GCA GGC GTA GTC AAA GAA GTT AAA GTT AAA GTC GGC GAC    210
Val Ala Gly Val Val Lys Glu Val Lys Val Lys Val Gly Asp
             60                  65                  70

AAA ATC TCT GAA GGT GGT TTG ATT GTC GTC GTT GAA GCT GAA    252
Lys Ile Ser Glu Gly Gly Leu Ile Val Val Val Glu Ala Glu
                 75                  80

GGC ACG GCA GCC GCT CCT AAA GCC GAA TCG GCT GCC GCC CCG    294
Gly Thr Ala Ala Ala Pro Lys Ala Glu Ser Ala Ala Ala Pro
 85                  90                  95

CGC AAG AAG CCC CTA AAC GTG CCG CTC CCT GCT CCG CAA GCC    336
Arg Lys Lys Pro Leu Asn Val Pro Leu Pro Ala Pro Gln Ala
    100                 105                 110

GCG CAA TTC GGC GGT TCT GCC GAT GCC GAG TAC GAT GTG GTC    378
Ala Gln Phe Gly Gly Ser Ala Asp Ala Glu Tyr Asp Val Val
        115                 120                 125

GTA TTG GGT GGC GGT CCC GGC GGT TAC TCC GCT GCA TTT GCC    420
Val Leu Gly Gly Gly Pro Gly Gly Tyr Ser Ala Ala Phe Ala
            130                 135                 140

GCT GCC GAT GAA GGC TTG AAA GTC GCC ATC GTC GAA CGT TAC    462
Ala Ala Asp Glu Gly Leu Lys Val Ala Ile Val Glu Arg Tyr
                145                 150

AAA ACT TTG GGC GGC GTT TGC CTG AAC GTC GGC TGT ATC CCT    504
```

-continued

```
Lys Thr Leu Gly Gly Val Cys Leu Asn Val Gly Cys Ile Pro
155                 160                 165

TCC AAA GCC TTG TTG CAC AAT GCC GCC GTT ATC GAC GAA GTG      546
Ser Lys Ala Leu Leu His Asn Ala Ala Val Ile Asp Glu Val
    170                 175                 180

CGC CAC TTG GCT GCC AAC GGT ATC AAA TAC CCC GAG CCG GAA      588
Arg His Leu Ala Ala Asn Gly Ile Lys Tyr Pro Glu Pro Glu
        185                 190                 195

CTC GAC ATC GAT ATG CTT CGC GCC TAC AAA GAC GGC GTA GTT      630
Leu Asp Ile Asp Met Leu Arg Ala Tyr Lys Asp Gly Val Val
            200                 205                 210

TCC CGC CTC ACG GGC GGT TTG GCA GGT ATG GCG AAA AGC CGT      672
Ser Arg Leu Thr Gly Gly Leu Ala Gly Met Ala Lys Ser Arg
                215                 220

AAA GTG GAC GTT ATC CAA GGC GAC GGG CAA TTC TTA GAT CCG      714
Lys Val Asp Val Ile Gln Gly Asp Gly Gln Phe Leu Asp Pro
225                 230                 235

CAC CAC TTG GAA GTG TCG CTG ACT GCC GGC GAC GCG TAC GAA      756
His His Leu Glu Val Ser Leu Thr Ala Gly Asp Ala Tyr Glu
    240                 245                 250

CAG GCA GCC CCT ACC GGC GAG AAA AAA ATC GTT GCC TTC AAA      798
Gln Ala Ala Pro Thr Gly Glu Lys Lys Ile Val Ala Phe Lys
        255                 260                 265

AAC TGT ATC ATT GCA GCA GGC AGC CGC GTA ACC AAA CTG CCT      840
Asn Cys Ile Ile Ala Ala Gly Ser Arg Val Thr Lys Leu Pro
            270                 275                 280

TTC ATT CCT GAA GAT CCG CGC ATC ATC GAT TCC AGC GGC GCA      882
Phe Ile Pro Glu Asp Pro Arg Ile Ile Asp Ser Ser Gly Ala
                285                 290

TTG GCT CTG AAA GAA GTA CCG GGC AAA CTG CTG ATT ATC GGC      924
Leu Ala Leu Lys Glu Val Pro Gly Lys Leu Leu Ile Ile Gly
295                 300                 305

GGC GGC ATT ATC GGC CTC GAG ATG GGT ACG GTT TAC AGC ACG      966
Gly Gly Ile Ile Gly Leu Glu Met Gly Thr Val Tyr Ser Thr
    310                 315                 320

CTG GGT TCG CGT TTG GAT GTG GTT GAA ATG ATG GAC GGC CTG     1008
Leu Gly Ser Arg Leu Asp Val Val Glu Met Met Asp Gly Leu
        325                 330                 335

ATG CAA GGC GCA GAC CGC GAT TTG GTA AAA GTA TGG CAA AAA     1050
Met Gln Gly Ala Asp Arg Asp Leu Val Lys Val Trp Gln Lys
            340                 345                 350

CAA AAC GAA TAC CGT TTT GAC AAC ATT ATG GTC AAC ACC AAA     1092
Gln Asn Glu Tyr Arg Phe Asp Asn Ile Met Val Asn Thr Lys
                355                 360

ACC GTT GCA GTT GAG CCG AAA GAA GAC GGC GTT TAC GTT ACC     1134
Thr Val Ala Val Glu Pro Lys Glu Asp Gly Val Tyr Val Thr
365                 370                 375

TTT GAA GGC GCG AAC GCC CCT AAA GAG CCG CAA CGC TAC GAT     1176
Phe Glu Gly Ala Asn Ala Pro Lys Glu Pro Gln Arg Tyr Asp
    380                 385                 390

GCC GTA TTG GTT GCC GCC GGC CGC GCG CCC AAC GGC AAA CTC     1218
Ala Val Leu Val Ala Ala Gly Arg Ala Pro Asn Gly Lys Leu
        395                 400                 405

ATC AGC GCG GAA AAA GCA GGC GTT GCC GTA ACC GAT CGC GGC     1260
Ile Ser Ala Glu Lys Ala Gly Val Ala Val Thr Asp Arg Gly
            410                 415                 420

TTC ATC GAA GTG GAC AAA CAA ATG CGT ACC AAT GTG CCG CAC     1302
Phe Ile Glu Val Asp Lys Gln Met Arg Thr Asn Val Pro His
                425                 430

ATC TAC GCC ATC GGC GAC ATC GTC GGT CAG CCG ATG TTG GCG     1344
Ile Tyr Ala Ile Gly Asp Ile Val Gly Gln Pro Met Leu Ala
435                 440                 445
```

|     |     |     |     |     |     |     |     |     |     |     |     |     |     | |
|-----|-----|-----|-----|-----|-----|-----|-----|-----|-----|-----|-----|-----|-----|-|
| CAC | AAA | GCC | GTT | CAC | GAA | GGC | CAC | GTT | GCC | GCC | GAA | AAC | TGC | 1386 |
| His | Lys | Ala | Val | His | Glu | Gly | His | Val | Ala | Ala | Glu | Asn | Cys | |
|     | 450 |     |     |     | 455 |     |     |     |     | 460 |     |     |     | |
| GCC | GGC | AAC | AAA | GCC | TAC | TTC | GAC | GCA | CGG | GTG | ATT | CCG | GGC | 1428 |
| Ala | Gly | Asn | Lys | Ala | Tyr | Phe | Asp | Ala | Arg | Val | Ile | Pro | Gly | |
|     |     | 465 |     |     |     |     | 470 |     |     |     |     | 475 |     | |
| GTT | GCC | TAC | ACT | TCC | CCC | GAA | GTG | GCG | TGG | GTG | GGC | GAA | ACC | 1470 |
| Val | Ala | Tyr | Thr | Ser | Pro | Glu | Val | Ala | Trp | Val | Gly | Glu | Thr | |
|     |     |     | 480 |     |     |     |     | 485 |     |     |     |     | 490 | |
| GAA | CTG | TCC | GCC | AAA | GCC | TCC | GCG | CGC | AAA | ATC | ACC | AAA | GCC | 1512 |
| Glu | Leu | Ser | Ala | Lys | Ala | Ser | Ala | Arg | Lys | Ile | Thr | Lys | Ala | |
|     |     |     |     | 495 |     |     |     |     | 500 |     |     |     |     | |
| AAC | TTC | CCG | TGG | GCG | GCT | TCC | GGC | CGT | GCG | ATT | GCC | AAC | GGT | 1554 |
| Asn | Phe | Pro | Trp | Ala | Ala | Ser | Gly | Arg | Ala | Ile | Ala | Asn | Gly | |
| 505 |     |     |     |     | 510 |     |     |     |     | 515 |     |     |     | |
| TGC | GAC | AAG | CCG | TTT | ACC | AAG | CTG | ATT | TTT | GAT | GCC | GAA | ACC | 1596 |
| Cys | Asp | Lys | Pro | Phe | Thr | Lys | Leu | Ile | Phe | Asp | Ala | Glu | Thr | |
|     | 520 |     |     |     |     | 525 |     |     |     |     | 530 |     |     | |
| GGC | CGC | ATC | ATC | GGC | GGC | GGC | ATT | GTC | GGT | CCG | AAC | GGT | GGC | 1638 |
| Gly | Arg | Ile | Ile | Gly | Gly | Gly | Ile | Val | Gly | Pro | Asn | Gly | Gly | |
|     |     | 535 |     |     |     |     | 540 |     |     |     |     | 545 |     | |
| GAT | ATG | ATC | GCG | AAG | TCT | GCC | TTG | CCA | TCG | AAA | TGG | GCT | GCG | 1680 |
| Asp | Met | Ile | Ala | Lys | Ser | Ala | Leu | Pro | Ser | Lys | Trp | Ala | Ala | |
|     |     |     | 550 |     |     |     |     | 555 |     |     |     |     | 560 | |
| ACA | CGT | GCA | GAC | ATC | GGC | AAA | ACC | ATC | CAC | CCG | CGC | CCG | ACC | 1722 |
| Thr | Arg | Ala | Asp | Ile | Gly | Lys | Thr | Ile | His | Pro | Arg | Pro | Thr | |
|     |     |     |     | 565 |     |     |     |     | 570 |     |     |     |     | |
| TTG | GGC | GAA | TCC | ATC | GGT | ATG | GCG | GCG | GAA | GTG | GCA | TTG | GGT | 1764 |
| Leu | Gly | Glu | Ser | Ile | Gly | Met | Ala | Ala | Glu | Val | Ala | Leu | Gly | |
| 575 |     |     |     |     | 580 |     |     |     |     | 585 |     |     |     | |
| ACT | TGT | ACC | GAC | CTG | CCT | CCG | CAA | AAG | AAA | AAA | TAA |     |     | 1800 |
| Thr | Cys | Thr | Asp | Leu | Pro | Pro | Gln | Lys | Lys | Lys |     |     |     | |
| 590 |     |     |     |     | 595 |     |     |     | 599 |     |     |     |     | |

ATCC GACTGAATAA ACAGCCGATA AGGT TTATTT GA                1836

( 2 ) INFORMATION FOR SEQ ID NO: 2:

( i ) SEQUENCE CHARACTERISTICS:
        ( A ) LENGTH:15 bases
        ( B ) TYPE: Nucleotide
        ( C ) STRANDEDNESS: single
        ( D ) TOPOLOGY: linear ( x i ) SEQUENCE DESCRIPTION: SEQ ID NO:2:

ATGCTAGATA AAAGA   15

( 2 ) INFORMATION FOR SEQ ID NO: 3:

( i ) SEQUENCE CHARACTERISTICS:
        ( A ) LENGTH: 25 amino acids
        ( B ) TYPE: Amino acid
        ( C ) STRANDEDNESS:single
        ( D ) TOPOLOGY:linear ( i i ) MOLECULE TYPE: Sequence N-terminal of P64k protein from outer
                membrane of N. meningitidis ( x i ) SEQUENCE DESCRIPTION: SEQ ID NO:3:

|     |     |     |     |     |     |     |     |     |     |     |     |     |
|-----|-----|-----|-----|-----|-----|-----|-----|-----|-----|-----|-----|-----|
| Met | Leu | Asp | Lys | Arg | Met | Ala | Leu | Val | Glu | Leu | Lys | Val | Pro | Asp |
| 1   |     |     |     | 5   |     |     |     |     | 10  |     |     |     |     | 15  |
| Ile | Gly | Gly | His | Glu | Asn | Val | Asp | Ile | Ile |
|     |     |     | 20  |     |     |     |     | 25  |     |

( 2 ) INFORMATION FOR SEQ ID NO: 4:

( i ) SEQUENCE CHARACTERISTICS:
    ( A ) LENGTH: 12 bases
    ( B ) TYPE: nucleotide
    ( C ) STRANDEDNESS: single
    ( D ) TOPOLOGY: linear ( x i ) SEQUENCE DESCRIPTION: SEQ ID NO:4:

CTAGATAAAA GA    12

( 2 ) INFORMATION FOR SEQ ID NO: 5:

( i ) SEQUENCE CHARACTERISTICS:
    ( A ) LENGTH: 8 bases
    ( B ) TYPE: nucleotide
    ( C ) STRANDEDNESS: single
    ( D ) TOPOLOGY: linear ( x i ) SEQUENCE DESCRIPTION: SEQ ID NO:5:

TCTTTTAT    8

( 2 ) INFORMATION FOR SEQ ID NO: 6:

( i ) SEQUENCE CHARACTERISTICS:
    ( A ) LENGTH: 221 amino acids
    ( B ) TYPE: Amino acid
    ( C ) STRANDEDNESS: single
    ( D ) TOPOLOGY: linear ( i i ) MOLECULE TYPE: Sequence which includes variable regions of
        P1.15 protein ( x i ) SEQUENCE DESCRIPTION: SEQ ID NO:6:

```
Leu Gln Leu Thr Glu Pro Pro Ser Lys Ser Gln Pro Gln Val Lys
 1               5                   10                  15

Val Thr Lys Ala Lys Ser Arg Ile Arg Thr Gln Ile Ser Asp Phe
                 20                  25                  30

Gly Ser Phe Ile Gly Phe Lys Gly Ser Glu Asp Leu Gly Glu Gly
                 35                  40                  45

Leu Lys Ala Val Trp Gln Leu Glu Gln Asp Val Ser Val Ala Gly
                 50                  55                  60

Gly Gly Ala Thr Gln Trp Gly Asn Arg Glu Ser Phe Val Gly Leu
                 65                  70                  75

Ala Gly Glu Phe Gly Thr Leu Arg Ala Gly Arg Val Ala Asn Gln
                 80                  85                  90

Phe Asp Asp Ala Ser Gln Ala Ile Asp Pro Trp Asp Ser Asn Asn
                 95                 100                 105

Asp Val Ala Ala Ser Gln Leu Gly Ile Phe Lys Arg His Asp Asp
                110                 115                 120

Met Pro Val Ser Val Arg Tyr Asp Ser Pro Asp Phe Ser Gly Phe
                125                 130                 135

Ser Gly Ser Val Gln Phe Val Pro Ile Gln Asn Ser Lys Ser Ala
                140                 145                 150

Tyr Thr Pro Ala Tyr His Tyr Thr Arg Gln Asn Asn Ala Asp Val
                155                 160                 165

Phe Val Pro Ala Val Val Gly Lys Pro Gly Ser Asp Val Tyr Val
                170                 175                 180

Ala Gly Leu Asn Tyr Lys Asn Gly Gly Phe Ala Gly Ser Tyr Ala
                185                 190                 195

Phe Lys Tyr Ala Arg His Ala Asn Val Gly Arg Asn Ala Phe Glu
                200                 205                 210

Leu Phe Leu Leu Gly Ser Thr Ser Asp Glu Ala
                215                 220
```

( 2 ) INFORMATION FOR SEQ ID NO: 7:

( i ) SEQUENCE CHARACTERISTICS:
　　　　( A ) LENGTH:6 amino acids
　　　　( B ) TYPE:Amino acid
　　　　( C ) STRANDEDNESS:single
　　　　( D ) TOPOLOGY:linear ( i i ) MOLECULE TYPE:Sequence corresponding to the fusion site
　　　　　　between N- terminal of P64k and P1.15

( x i ) SEQUENCE DESCRIPTION: SEQ ID NO:7:

```
Gly  Asp  Ala  Leu  Gln  Leu
 1              5
```

( 2 ) INFORMATION FOR SEQ ID NO: 8:

( i ) SEQUENCE CHARACTERISTICS:
　　　　( A ) LENGTH:19 bases
　　　　( B ) TYPE:nucleotide
　　　　( C ) STRANDEDNESS:single
　　　　( D ) TOPOLOGY:linear ( i i ) MOLECULE TYPE:Sequence corresponding to the fusion of
　　　　　　N-terminal from gene M-6 and from gene P1.15

( x i ) SEQUENCE DESCRIPTION: SEQ ID NO:8:

```
GGCGACGCGC  TGCAGTTGA        19
```

( 2 ) INFORMATION FOR SEQ ID NO: 9:

( i ) SEQUENCE CHARACTERISTICS:
　　　　( A ) LENGTH:6 amino acids
　　　　( B ) TYPE:Amino acid
　　　　( C ) STRANDEDNESS:single
　　　　( D ) TOPOLOGY:linear ( i i ) MOLECULE TYPE:Sequence corresponding to the fusion site
　　　　　　between C- terminal of P64k and P1.15

( x i ) SEQUENCE DESCRIPTION: SEQ ID NO:9:

```
Glu  Ala  Asn  Ala  Tyr  Glu
 1              5
```

( 2 ) INFORMATION FOR SEQ ID NO: 10:

( i ) SEQUENCE CHARACTERISTICS:
　　　　( A ) LENGTH:18 bases
　　　　( B ) TYPE:nucleotide
　　　　( C ) STRANDEDNESS:single
　　　　( D ) TOPOLOGY:linear ( i i ) MOLECULE TYPE:Sequence corresponding to the fusion of
　　　　　　C-terminal from gene M-6 and from gene P1.15

( x i ) SEQUENCE DESCRIPTION: SEQ ID NO:10:

```
GAAGCCAACG  CGTACGAA        18
```

( 2 ) INFORMATION FOR SEQ ID NO: 11:

( i ) SEQUENCE CHARACTERISTICS:
　　　　( A ) LENGTH: 111 amino acids
　　　　( B ) TYPE:Amino acid
　　　　( C ) STRANDEDNESS:single
　　　　( D ) TOPOLOGY:linear ( i i ) MOLECULE TYPE:p64k N-terminal comprising homology region with
　　　　　　" lypoil binding site"from E. coli Acetyl transferase ( x i ) SEQUENCE DESCRIPTION: SEQ ID NO:11:

```
Met  Ala  Leu  Val  Glu  Leu  Lys  Val  Pro  Asp  Ile  Gly  Gly  His  Glu
```

-continued

|   | 1 |   |   | 5 |   |   |   |   | 10 |   |   |   |   | 15 |   |
|---|---|---|---|---|---|---|---|---|----|---|---|---|---|----|---|

Asn Val Asp Ile Ile Ala Val Glu Val Asn Val Gly Asp Thr Ile
 1           5              20         25              30

Ala Val Asp Asp Thr Leu Ile Thr Leu Glu Thr Asp Lys Ala Thr
                 35              40                  45

Met Asp Val Pro Ala Glu Val Ala Gly Val Val Lys Glu Val Lys
                 50              55                  60

Val Lys Val Gly Asp Lys Ile Ser Glu Gly Gly Leu Ile Val Val
                 65              70                  75

Val Glu Ala Glu Gly Thr Ala Ala Ala Pro Lys Ala Glu Ser Ala
                 80              85                  90

Ala Ala Pro Arg Lys Lys Pro Leu Lys Cys Arg Trp Val Pro Gln
                 95              100                 105

Ala Ala Gln Phe Gly Gly
                 110

(2) INFORMATION FOR SEQ ID NO: 12:

(i) SEQUENCE CHARACTERISTICS:
      (A) LENGTH:112 amino acids
      (B) TYPE:Amino acid
      (C) STRANDEDNESS:single
      (D) TOPOLOGY:linear (ii) MOLECULE TYPE: "lypoil binding site" from E. coli
        Acetyl- transferase (xi) SEQUENCE DESCRIPTION: SEQ ID NO:12:

Val Lys Glu Val Asn Val Pro Asp Ile Gly Gly Asp Glu Val Glu
 1           5              10                  15

Val Thr Glu Val Met Val Lys Val Gly Asp Lys Val Ala Ala Glu
                 20              25                  30

Gln Ser Leu Ile Thr Val Glu Gly Asp Lys Ala Ser Met Glu Val
                 35              40                  45

Pro Ala Pro Phe Ala Gly Val Val Lys Glu Leu Lys Val Asn Val
                 50              55                  60

Gly Asp Lys Val Lys Thr Gly Ser Leu Ile Met Ile Phe Glu Val
                 65              70                  75

Glu Gly Ala Ala Pro Ala Ala Ala Pro Ala Lys Gln Glu Ala Ala
                 80              85                  90

Ala Pro Ala Pro Ala Ala Lys Ala Glu Ala Pro Ala Ala Ala Pro
                 95              100                 105

Ala Ala Lys Ala Glu Gly Lys
                 110

(2) INFORMATION FOR SEQ ID NO: 13:

(i) SEQUENCE CHARACTERISTICS:
      (A) LENGTH:481 amino acids
      (B) TYPE:Amino acid
      (C) STRANDEDNESS:single
      (D) TOPOLOGY:linear (ii) MOLECULE TYPE: P64k fragment comprising the homology region
        with Lipoamide Dehydrogenase from E. coli (xi) SEQUENCE DESCRIPTION: SEQ ID NO:13:

Ser Ala Asp Ala Glu Tyr Asp Val Val Val Leu Gly Gly Gly Pro
 1           5              10                  15

Gly Gly Tyr Ser Ala Ala Phe Ala Ala Ala Asp Glu Gly Leu Lys
                 20              25                  30

Val Ala Ile Val Glu Arg Tyr Lys Thr Leu Gly Gly Val Cys Leu

```
                              35                          40                          45
Asn Val Gly Cys Ile Pro Ser Lys Ala Leu Leu His Asn Ala Ala
                      50                          55                          60
Val Ile Asp Glu Val Arg His Leu Ala Ala Asn Gly Ile Lys Tyr
                      65                          70                          75
Pro Glu Pro Ala Leu Asp Ile Asp Met Leu Arg Ala Tyr Lys Asp
                      80                          85                          90
Gly Val Val Ser Arg Leu Thr Gly Phe Gly Arg Tyr Gly Glu Lys
                      95                         100                         105
Arg Lys Val Asp Val Ile Gln Gly Asp Gly Gln Phe Leu Asp Pro
                     110                         115                         120
His His Leu Glu Val Ser Leu Thr Ala Gly Asp Ala Tyr Glu Gln
                     125                         130                         135
Ala Ala Pro Thr Gly Glu Lys Lys Ile Val Ala Phe Lys Asn Cys
                     140                         145                         150
Ile Ile Ala Ala Gly Ser Arg Val Thr Lys Leu Pro Phe Ile Pro
                     155                         160                         165
Glu Asp Pro Arg Ile Ile Asp Ser Ser Gly Ala Leu Ala Leu Lys
                     170                         175                         180
Glu Val Pro Gly Lys Leu Leu Ile Ile Gly Gly Gly Ile Ile Gly
                     185                         190                         195
Leu Glu Met Gly Thr Val Tyr Ser Thr Leu Gly Ser Arg Leu Asp
                     200                         205                         210
Val Val Glu Met Met Asp Gly Leu Met Gln Gly Ala Asp Arg Asp
                     215                         220                         225
Leu Val Lys Val Trp Gln Lys Gln Asn Glu Tyr Arg Phe Asp Asn
                     230                         235                         240
Ile Met Val Asn Thr Lys Thr Val Ala Val Glu Pro Lys Glu Asp
                     245                         250                         255
Gly Val Tyr Val Thr Phe Glu Gly Ala Asn Pro Pro Lys Glu Pro
                     260                         265                         270
Gln Arg Tyr Asp Ala Val Leu Val Ala Ala Gly Arg Ala Pro Asn
                     275                         280                         285
Gly Lys Leu Ile Ser Ala Glu Lys Ala Gly Val Ala Val Thr Asp
                     290                         295                         300
Arg Gly Phe Ile Glu Val Asp Lys Gln Met Arg Thr Asn Val Pro
                     305                         310                         315
His Ile Tyr Ala Ile Gly Asp Ile Val Gly Gln Pro Met Leu Ala
                     320                         325                         330
His Lys Ala Val His Glu Gly His Val Ala Ala Glu Asn Cys Ala
                     335                         340                         345
Gly Thr Lys Ala Tyr Phe Asp Ala Ala Val Ile Pro Gly Val Ala
                     350                         355                         360
Tyr Thr Ser Pro Glu Val Ala Trp Val Gly Glu Thr Glu Leu Ser
                     365                         370                         375
Ala Lys Arg Pro Ala Gly Lys Ile Thr Lys Ala Asn Phe Pro Trp
                     380                         385                         390
Ala Ala Ser Gly Arg Ala Ile Ala Asn Gly Cys Asp Lys Pro Phe
                     395                         400                         405
Thr Lys Leu Ile Phe Asp Ala Glu Thr Gly Arg Ile Ile Gly Gly
                     410                         415                         420
Gly Ile Val Gly Pro Asn Gly Gly Asp Met Ile Ala Lys Ser Ala
                     425                         430                         435
    Leu Pro Ser Lys Leu Gly Cys Asp Ala Ala Asp Val Gly Lys Thr
                         440                         445                         450
```

```
            Ile His Pro Arg Pro Thr Leu Gly Glu Ser Ile Gly Met Ala Ala
                        455                 460                 465

Glu Val Ala Leu Gly Thr Cys Thr Asp Leu Pro Pro Gln Lys Lys
                        470                 475                 480

Lys
```

( 2 ) INFORMATION FOR SEQ ID NO: 14:

( i ) SEQUENCE CHARACTERISTICS:
        ( A ) LENGTH:472 bases
        ( B ) TYPE:Amino acid
        ( C ) STRANDEDNESS:single
        ( D ) TOPOLOGY:linear ( i i ) MOLECULE TYPE: Segment of E. coli Lipoamide Dehydrogenase with
          homology to P64k protein ( x i ) SEQUENCE DESCRIPTION: SEQ ID NO:14:

```
            Ser Thr Glu Ile Lys Thr Gln Val Val Leu Gly Ala Gly Pro
             1               5                  10                  15

Ala Gly Tyr Ser Ala Ala Phe Arg Cys Ala Asp Leu Gly Leu Glu
                         20                  25                  30

Thr Val Ile Val Glu Arg Tyr Asn Thr Leu Gly Gly Val Cys Leu
                         35                  40                  45

Asn Val Gly Cys Ile Pro Ser Lys Ala Leu Leu His Val Ala Lys
                         50                  55                  60

Val Ile Glu Glu Ala Lys Ala Leu Ala Glu His Gly Ile Val Phe
                         65                  70                  75

Gly Glu Pro Lys Thr Asp Ile Asp Lys Ile Thr Trp Lys Glu Lys
                         80                  85                  90

Val Ile Asn Gln Leu Thr Gly Gly Leu Ala Gly Met Ala Lys Gly
                         95                 100                 105

Arg Lys Val Lys Val Val Asn Gly Leu Gly Lys Phe Thr Gly Ala
                        110                 115                 120

Asn Thr Leu Glu Val Glu Gly Glu Asn Gly Lys Thr Val Ile Asn
                        125                 130                 135

Phe Asp Asn Ala Ile Ile Ala Ala Gly Ser Arg Pro Ile Gln Leu
                        140                 145                 150

Pro Phe Ile Pro His Glu Asp Pro Arg Ile Trp Asp Ser Thr Asp
                        155                 160                 165

Ala Leu Glu Leu Lys Glu Val Pro Glu Arg Leu Leu Val Met Gly
                        170                 175                 180

Gly Gly Ile Ile Gly Leu Glu Met Gly Thr Val Tyr His Ala Leu
                        185                 190                 195

Gly Ser Gln Ile Asp Val Val Glu Met Phe Asp Gln Val Ile Pro
                        200                 205                 210

Ala Ala Asp Lys Asp Ile Val Lys Val Phe Thr Lys Arg Ile Ser
                        215                 220                 225

Lys Lys Phe Asn Leu Met Leu Glu Thr Lys Val Thr Ala Val Glu
                        230                 235                 240

Ala Lys Glu Asp Gly Ile Tyr Val Thr Met Glu Gly Lys Lys Ala
                        245                 250                 255

Pro Ala Glu Pro Gln Arg Tyr Asp Ala Val Leu Val Ala Ile Gly
                        260                 265                 270

Arg Val Pro Asn Gly Lys Asn Leu Asp Ala Gly Lys Ala Gly Val
                        275                 280                 285

Glu Val Asp Asp Arg Gly Phe Ile Arg Val Asp Lys Gln Leu Arg
                        290                 295                 300
```

|     |     |     |     |     |     |     |     |     |     |     |     |     |     |     |
|-----|-----|-----|-----|-----|-----|-----|-----|-----|-----|-----|-----|-----|-----|-----|
| Thr | Asn | Val | Pro | His | Ile | Phe | Ala | Ile | Gly | Asp | Ile | Val | Gly | Gln |
|     |     |     |     |     | 305 |     |     |     | 310 |     |     |     |     | 315 |
| Pro | Met | Leu | Ala | His | Lys | Gly | Val | His | Glu | Gly | His | Val | Ala | Ala |
|     |     |     |     | 320 |     |     |     |     | 325 |     |     |     |     | 330 |
| Glu | Val | Ile | Ala | Gly | Lys | Lys | His | Tyr | Phe | Asp | Pro | Lys | Val | Ile |
|     |     |     |     | 335 |     |     |     |     | 340 |     |     |     |     | 345 |
| Pro | Ser | Ile | Ala | Tyr | Thr | Glu | Pro | Glu | Val | Ala | Trp | Val | Gly | Leu |
|     |     |     |     | 350 |     |     |     |     | 355 |     |     |     |     | 360 |
| Thr | Glu | Lys | Glu | Ala | Lys | Glu | Lys | Gly | Ile | Ser | Tyr | Glu | Thr | Ala |
|     |     |     |     | 365 |     |     |     |     | 370 |     |     |     |     | 375 |
| Thr | Phe | Pro | Trp | Ala | Ala | Ser | Gly | Arg | Ala | Ile | Ala | Ser | Asp | Cys |
|     |     |     |     | 380 |     |     |     |     | 385 |     |     |     |     | 390 |
| Ala | Asp | Gly | Met | Thr | Lys | Leu | Ile | Phe | Asp | Lys | Glu | Ser | His | Arg |
|     |     |     |     | 395 |     |     |     |     | 400 |     |     |     |     | 405 |
| Val | Ile | Gly | Gly | Ala | Ile | Val | Gly | Thr | Asn | Gly | Gly | Glu | Leu | Leu |
|     |     |     |     | 410 |     |     |     |     | 415 |     |     |     |     | 420 |
| Gly | Glu | Ile | Gly | Leu | Ala | Ile | Glu | Met | Gly | Cys | Asp | Ala | Glu | Asp |
|     |     |     |     | 425 |     |     |     |     | 430 |     |     |     |     | 435 |
| Ile | Ala | Leu | Thr | Ile | His | Ala | His | Pro | Thr | Leu | His | Glu | Ser | Val |
|     |     |     |     | 440 |     |     |     |     | 445 |     |     |     |     | 450 |
| Gly | Leu | Ala | Ala | Glu | Val | Phe | Glu | Gly | Ser | Ile | Thr | Asp | Leu | Pro |
|     |     |     |     | 455 |     |     |     |     | 460 |     |     |     |     | 465 |
| Asn | Pro | Lys | Ala | Lys | Lys | Lys |     |     |     |     |     |     |     |     |
|     |     |     |     | 470 |     |     |     |     |     |     |     |     |     |     |